(12) United States Patent
Kikuchi

(10) Patent No.: US 6,279,387 B1
(45) Date of Patent: Aug. 28, 2001

(54) MOISTURE METER, ELECTRONIC WEIGHING MACHINE FOR MOISTURE METER, FILTER FOR MOISTURE METER, AND MOISTURE ADSORPTION UNIT FOR MOISTURE METER

(75) Inventor: Fumihide Kikuchi, Tokyo (JP)

(73) Assignee: Kett Electric Laboratory, Tokyo (JP)

( * ) Notice: Subject to any disclaimer, the term of this patent is extended or adjusted under 35 U.S.C. 154(b) by 0 days.

(21) Appl. No.: 09/066,666

(22) Filed: Apr. 28, 1998

(30) Foreign Application Priority Data

| May 2, 1997 | (JP) | 9-114665 |
| May 2, 1997 | (JP) | 9-114666 |
| May 2, 1997 | (JP) | 9-114667 |
| May 2, 1997 | (JP) | 9-114668 |
| May 2, 1997 | (JP) | 9-114669 |

(51) Int. Cl.[7] ............... G01G 19/00; G01N 22/04
(52) U.S. Cl. ............... 73/76; 73/73; 73/29.01; 73/29.04; 374/14; 177/61
(58) Field of Search ............... 73/76, 73, 335.06, 73/29.01, 29.04; 374/14; 177/61

(56) References Cited

U.S. PATENT DOCUMENTS

| 1,455,263 | * | 5/1923 | Oberfell | 73/29.01 |
| 2,097,650 | * | 11/1937 | Stampe | 73/29.04 |
| 2,379,045 | * | 6/1945 | Sturgis | 73/76 |
| 2,420,648 | * | 8/1947 | Bolton | 73/29.04 |
| 4,838,705 | | 6/1989 | Byers, Jr. et al. | 73/76 |
| 5,377,532 | * | 1/1995 | Urza | 73/73 |

* cited by examiner

Primary Examiner—Hezron Williams
Assistant Examiner—Michael Cygan
(74) Attorney, Agent, or Firm—Wenderoth, Lind & Ponack, L.L.P.

(57) ABSTRACT

An electronic weighing machine for a moisture meter not only measures the amount of moisture in the test sample, but also measures the mass of the test sample itself. In addition, the present invention is related to a heat drying type moisture meter, a filter for the moisture meter and a moisture adsorption unit for the moisture meter. The electronic weighing machine for the moisture meter is used with the moisture meter which is equipped with a heating section for introducing the carrier gas into it and heating the test sample, a moisture adsorption section for adsorbing the vaporized moisture from the carrier gas flowing out of the heating section, and an electronic weighing section for determining the increase in mass of the moisture adsorption section. The electronic weighing section has a test sample weighing section and a section for measuring the mass of the collected vaporized moisture in the weighing arm of the electronic weighing unit.

19 Claims, 12 Drawing Sheets

F I G. 2
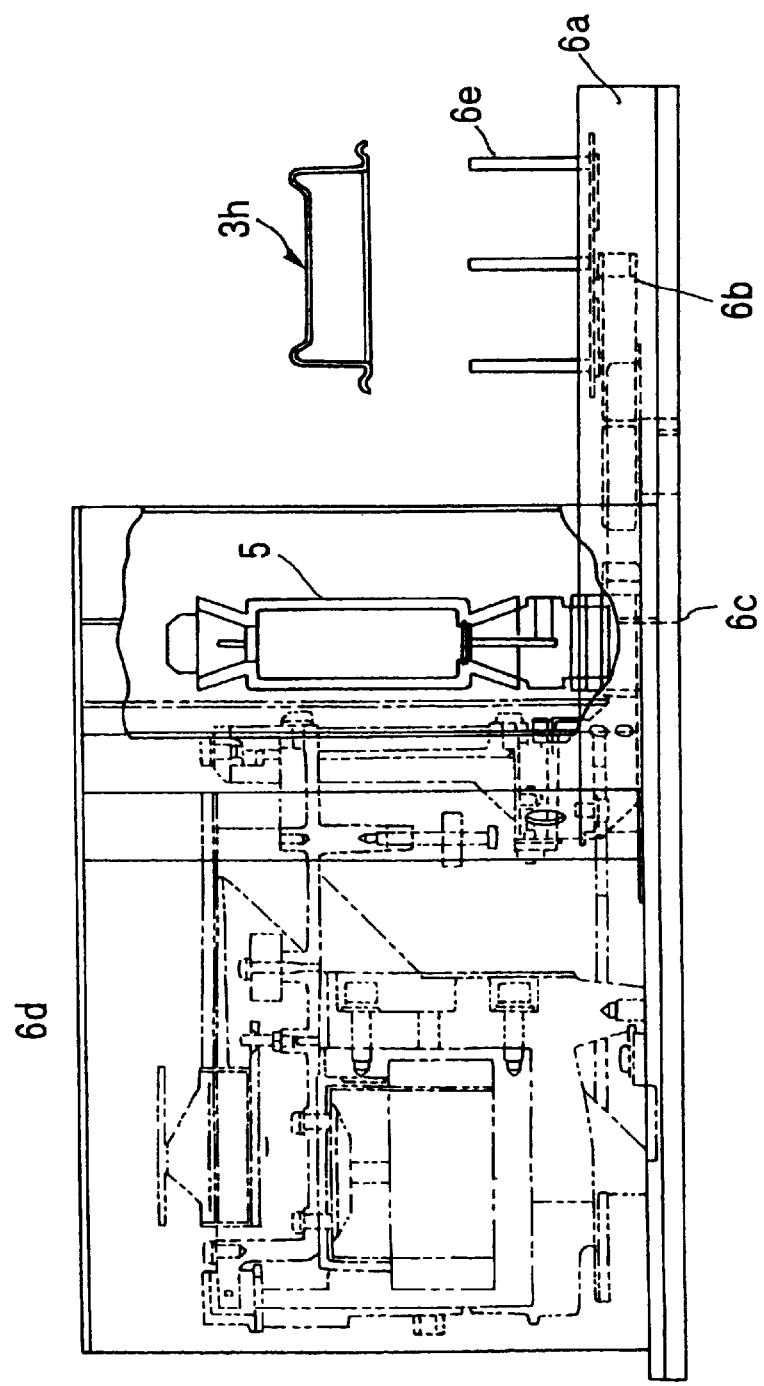

F I G . 3
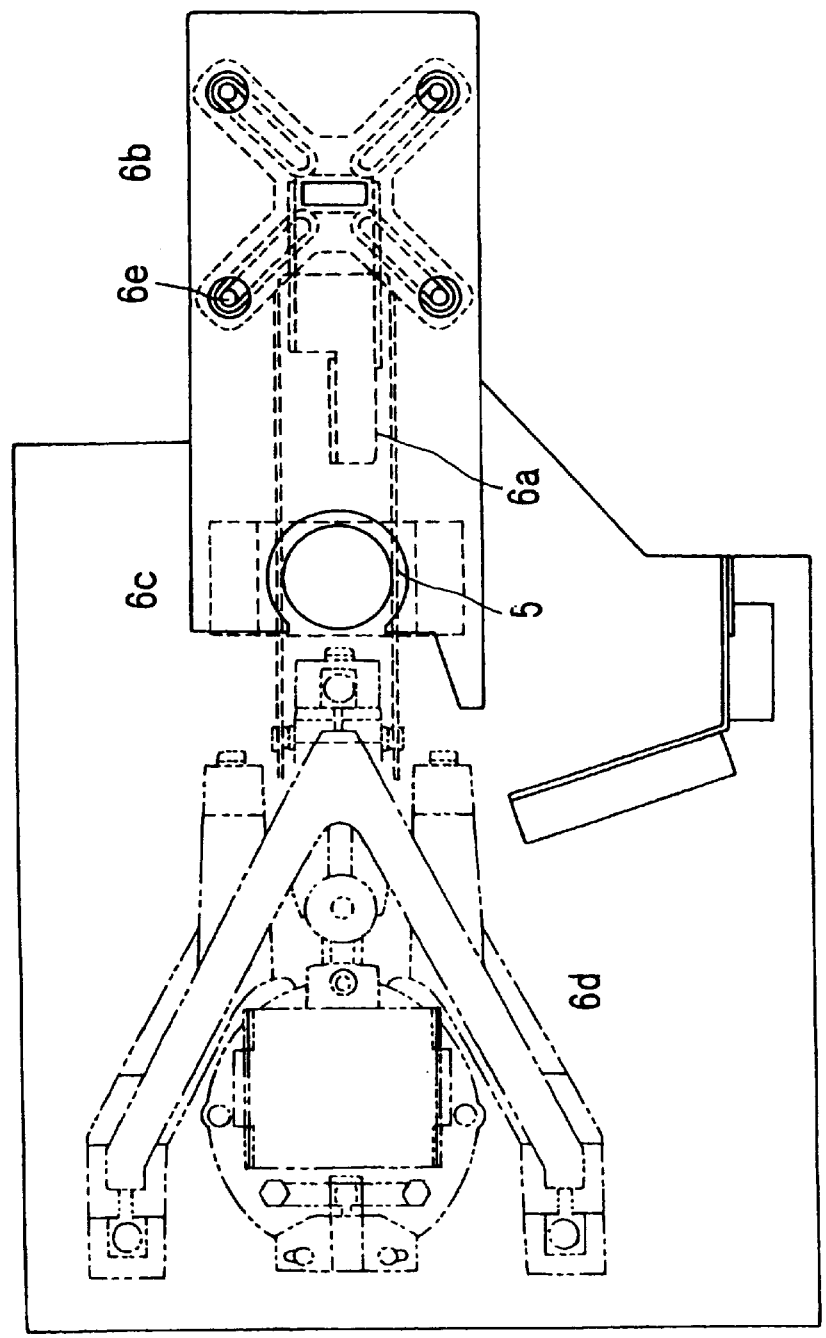

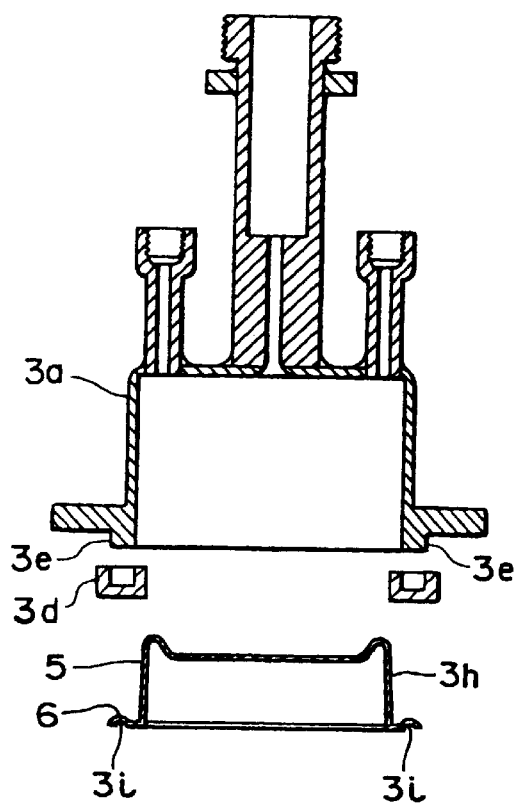
F I G. 5
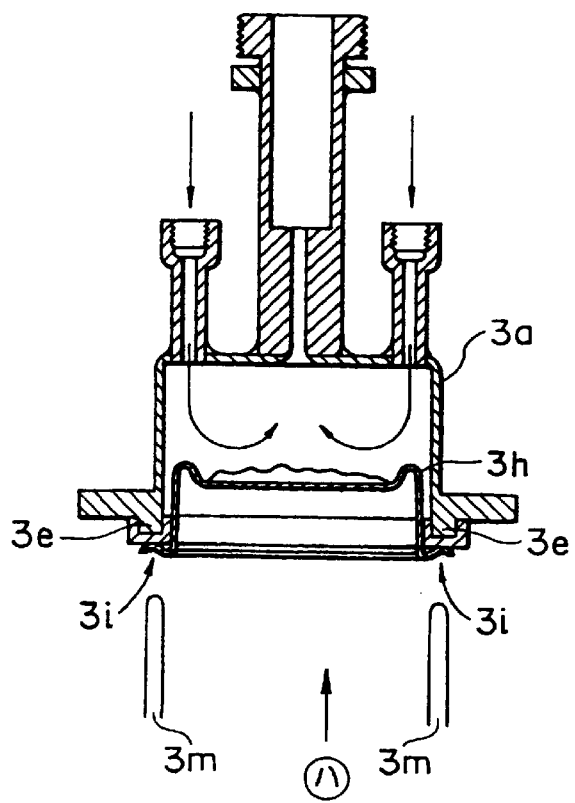
F I G. 6

F I G . 11
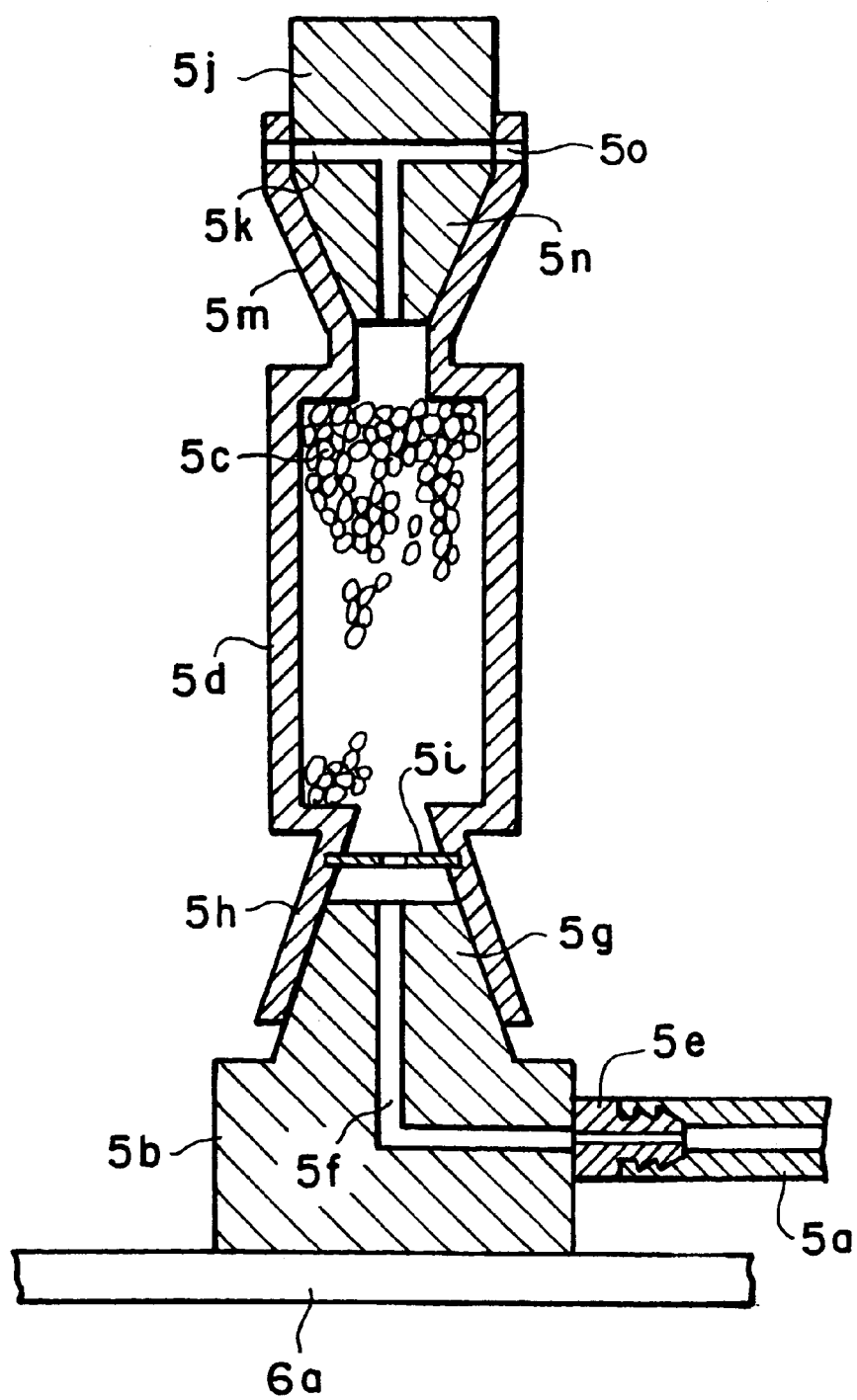

F I G. 12
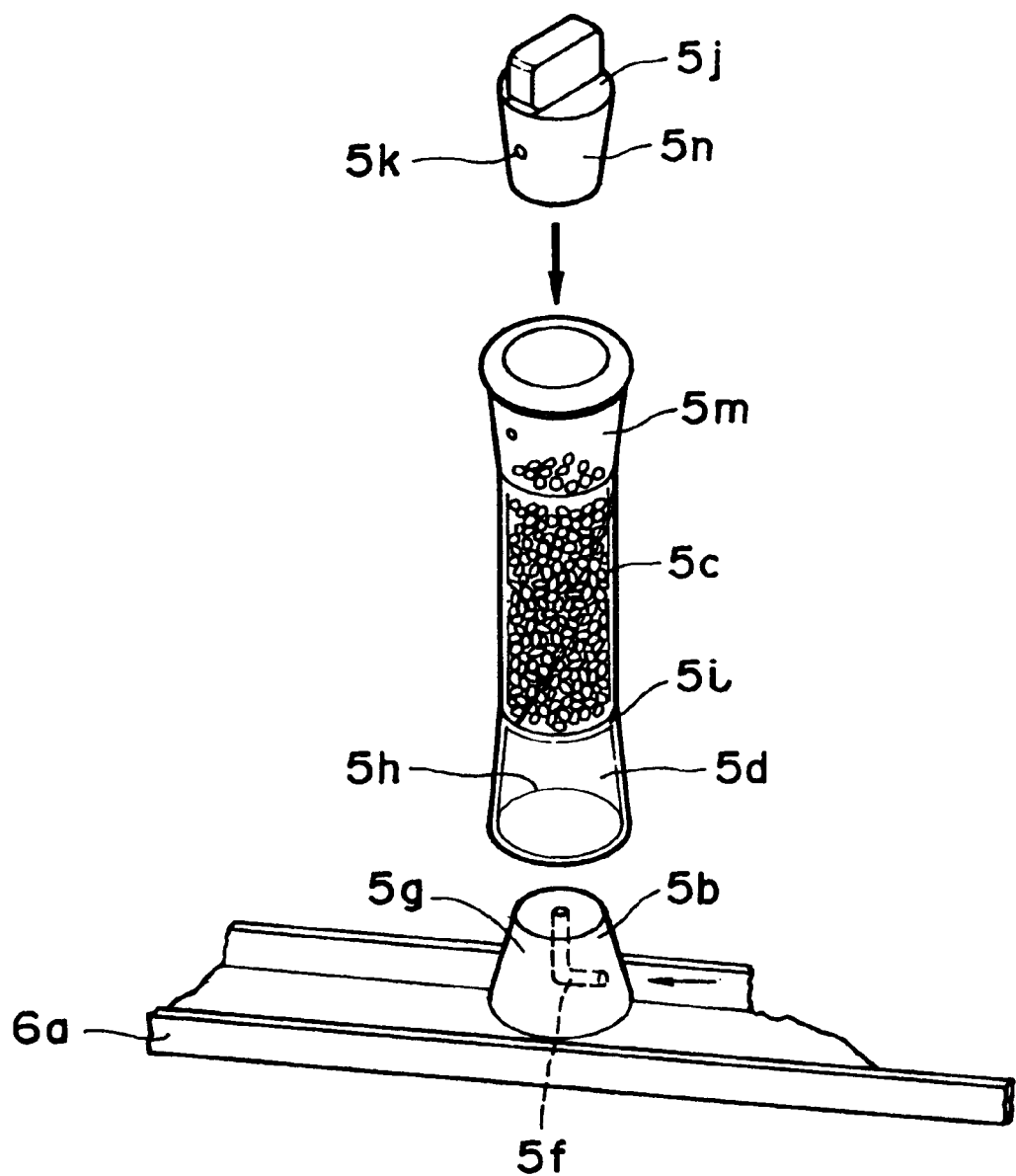

when determination is made      when determination is not made
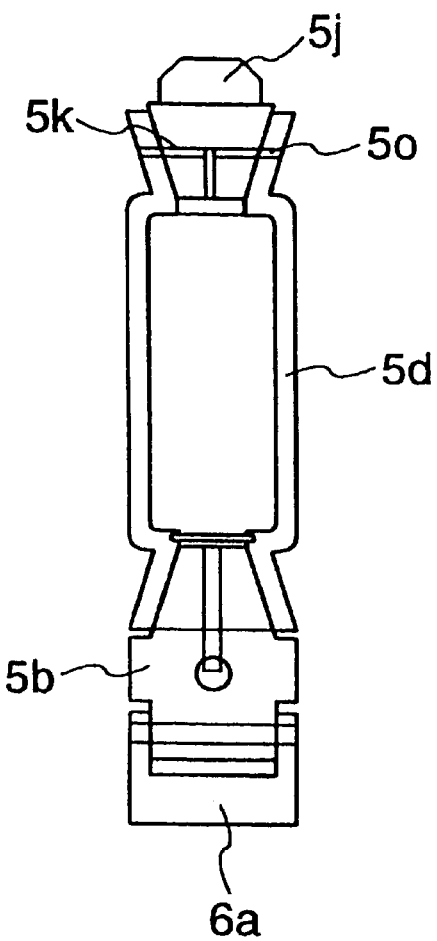
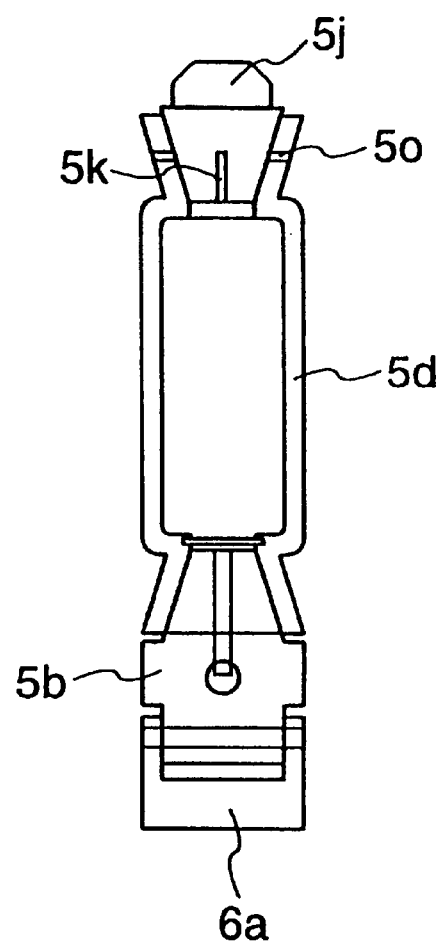
F I G. 13A                    F I G. 13B

MOISTURE METER, ELECTRONIC WEIGHING MACHINE FOR MOISTURE METER, FILTER FOR MOISTURE METER, AND MOISTURE ADSORPTION UNIT FOR MOISTURE METER

BACKGROUND OF THE INVENTION

FIELD OF THE INVENTION

The present invention is related to an electronic weighing machine for a moisture meter. Specifically, it relates to an electronic weighing machine for the moisture meter that can measure not only the amount of moisture in a test sample, but also the mass of the test sample itself.

The present invention is also related to a heat drying type moisture meter that can accurately determine an extremely low moisture content of the test sample by vaporizing the moisture in the test sample by heating, selecting the moisture from the vaporized moisture and gases, and collecting only the moisture for measurement.

The present invention is also related to a heat drying type moisture meter that can determine an extremely low moisture content of the test sample by vaporizing the moisture in the test sample by heating, selecting the moisture from the vaporized moisture and gases, and collecting only the moisture for measurement.

The present invention is also related to a filter for the moisture meter that allows the adsorbent material in it to be easily replaced with new material.

The present invention is also related to a moisture adsorption unit for the moisture meter. Specifically, it relates to a filter configured so that during replacement of the adsorbent material for collecting the vaporized moisture with fresh material, no external force is applied to the weighing arm in the electronic weighing machine for determining the moisture content of the test sample.

PRIOR ART

As a conventional high precision method of determining the moisture content of a solid or liquid, the Karl Fischer (KF) method is widely known. In the KF method, the Karl Fischer reagent consisting of iodine, sulfur dioxide, pyridine, and methanol quantitatively reacts with water. However, in determining the moisture content by using the KF method, various modifications may be required, depending upon the substance under test. Furthermore, to determine the exact moisture content, a significantly high degree of skill has been required. In addition, in making the determination, a special reagent and glass container have been required.

To solve these problems, moisture meters of a heat drying type have been developed. Such a heat drying type moisture meter, as that given in the gazette Laid-Open Publication No. 7-126961/1995, is equipped with a gas introduction section for producing the carrier gas, a heating section for introducing the carrier gas from this gas introduction section to heat the test sample, a moisture collection section for collecting the vaporized moisture from the carrier gas flowing out of this heating section, and an electronic weighing unit for determining the increase in the mass of the moisture collection section, determining the moisture content of the test sample by heating the test sample to vaporize the moisture in it, and collecting and measuring this vaporized moisture.

As a conventional high precision method of determining the moisture content of a solid or liquid, the Karl Fischer (KF) method is widely known. In the KF method, the Karl Fischer reagent consisting of iodine, sulfur dioxide, pyridine, and methanol quantitatively reacts with water. However, in determining the moisture content by using the KF method, various modifications may be required, depending upon the substance under test. In addition, the KF reagent reacts with substances other than $H_2O$. Therefore, to determine the exact moisture content, a significantly high degree of skill has been required. In addition, in making the determination, a special reagent and glass container have been required.

To solve these problems, moisture meters of a heat drying type have been developed. Such a heat drying type moisture meter, as that given in the gazette Laid-Open Publication No. 7-12696/1995, is equipped with a gas introduction section for producing the carrier gas, a heating section for introducing the carrier gas from this gas introduction section to heat the test sample, a moisture collection section for collecting the vaporized moisture from the carrier gas flowing out of this heating section, and an electronic weighing unit for determining the increase in mass of the moisture collection section, determining the moisture content of the test sample by heating the test sample to vaporize the moisture in it, and collecting and measuring this vaporized moisture.

To determine the moisture content of the test sample with higher accuracy, the gazette Laid-Open Publication No. 7-12698/1995 gives a moisture meter that is provided with a filter before the moisture collection section.

As a moisture collection unit for such a moisture meter, a moisture collection unit with which the carrier gas introduction tube is directly connected to the cell charged with adsorbent has been used. However, because the carrier gas introduction tube is directly connected to the cell body, the tube is twisted during replacement of the adsorbent material with fresh material, which results in variations in measurement by the electronic weighing machine.

To allow the adsorbent to be replaced with fresh material without adversely affecting the tube for introduction of the carrier gas, a moisture adsorption unit with which the tube is connected with the cell body through the cell base (as given in the gazette Laid-Open Publication No. 7-12697/1995) has been offered in recent years. With such a moisture adsorption unit, replacement of the adsorbent with fresh material can be made by removing the cell body from the cell base, replacing the adsorbent in the cell body, and reconnecting the cell body to the cell base. This has solved problems such as that of the tube being twisted during replacement of the adsorbent, and substantially improved the determination efficiency. However, such a moisture adsorption unit has presented the following problems.

In conventional electronic weighing machines for heat drying type moisture meters, the amount of the vaporized moisture can be measured, while the mass of the test sample cannot be measured. Therefore, the mass of the test sample must be accurately measured outside the moisture meter. Thus, a separate electronic weighing machine having the same accuracy as that of the moisture meter must be provided.

In addition, with moisture meters having such a conventional electronic weighing machine, measurement of the mass of the test sample with the electronic weighing machine installed outside the moisture meter must be followed by moving the test sample into the moisture meter. This results in adsorption of the atmospheric moisture or discharge of the moisture in the test sample during movement of the test sample. Thus, an error due to the measuring environment and a personal difference in measurement tend to be caused, so that making a determination with high accuracy becomes impossible.

Further, in calculating the moisture content, the operator must enter the mass of the test sample measured outside the moisture meter in the moisture meter, and an electronic weighing machine having the same accuracy as that of the moisture meter must separately be provided. This creates problems of workability and cost having been presented.

Then, the purpose of the present invention is to offer an electronic weighing machine for the moisture meter that can measure not only the amount of the moisture vaporized from the test sample, but also the mass of the test sample itself.

In conventional heat drying type moisture meters, the cylindrical heating tube is of a horizontal type. Thus, opening the cover of the heating tube during insertion of the test sample allows the carrier gas to flow out from the upper portion of the heating tube while the atmosphere flows in from the lower portion of the tube, which results in errors being caused. In addition, with a heating tube that is long sideways, many portions are not heated, thus, so that the moisture vaporized from the test sample tends to be liquefied. Furthermore, because the carrier gas flowing-out port is provided in the middle of the horizontal heating tube, the carrier gas and other gases accumulated in the end portions of the heating tube cannot completely flow out.

In addition, with the heating section of a conventional heat drying type moisture meter, the mass of the test sample must be accurately measured outside the moisture meter. Thus an electronic weighing machine having the same accuracy as that of the moisture meter must be separately provided outside the moisture meter. In moving the test sample from the outside of the moisture meter into it, the moisture can be adsorbed or discharged, which tends to cause errors due to the measuring environment.

Further, with the heating section of such a moisture meter, the carrier gas is introduced from a single port. Thus, all carrier gas can flow out and the carrier gas cannot effectively flow over the surface of the test sample, resulting in errors being caused and a long time being taken for making a measurement.

Further, with conventional heat drying type moisture meters, the adsorbent in the filter and that in the moisture adsorption section cannot easily be replaced with fresh material. In addition, because the filter section and the moisture adsorption section are made of stainless steel, their contents are invisible from the outside.

Therefore, one purpose of the present invention is to offer a moisture meter which eliminates the need for a special skill, can be easily operated, and with which errors due to the effect of the external environment cannot easily be caused. As a result, the moisture content can be determined with extremely high accuracy. Another purpose is to offer a moisture meter which minimizes the personal difference in measurement and allows the moisture content to be determined in a short time.

With conventional heat drying type moisture meters as stated above, the carrier gas is introduced from a single port. Thus, all carrier gas can flow out and the carrier gas cannot effectively flow over the surface of the test sample. Especially, when the heating tube is of horizontal type, the carrier gas flowing-out port is provided in the middle of the horizontal heating tube. Thus, by introducing the carrier gas from a single port, the carrier gas and other gas accumulated in the end portions of the heating tube cannot completely flow out.

Such a problem in the carrier gas flowing out prevents accurate determination of the moisture content, and can extend the measuring time.

In addition, with the heating section of a conventional heat drying type moisture meter, the mass of the test sample must be accurately measured outside the moisture meter. Thus, an electronic weighing machine having the same accuracy as that of the moisture meter must be separately provided outside the moisture meter. Furthermore, in moving the test sample from the outside of the moisture meter into it, the moisture can be adsorbed or discharged, which tends to cause errors due to the measuring environment.

Further, with conventional heat drying type moisture meters, the adsorbent in the filter and that in the moisture adsorption section cannot easily be replaced with fresh material. Because the filter section and the moisture adsorption section are made of stainless steel, their contents are invisible from the outside.

Therefore, one purpose of the present invention is to offer a moisture meter which eliminates the need for a special skill, can be easily operated, and with which the personal difference in measurement is minimized and the moisture content can be determined in a short time. Another purpose is to offer a moisture meter with which errors due to the effect of the external environment cannot easily be caused, so that the moisture content can be determined with extremely high accuracy.

With regard to the filter for such a heat drying type moisture meter, to prevent the atmospheric moisture from entering the inside of the filter, the method that joins the filter container with the top cover by tightening the screw is adopted. Thus, to remove the top cover from the filter container to replace the adsorbent in the filter with fresh material, the top cover must be turned. Because this turning of the top cover imposes a great load on (twists) the tube connected to the top cover, the tube must be removed before removing the top cover during replacement of the adsorbent in order to prevent the tube surface from being cracked and damaged by twisting the tube.

Consequently, the operation of replacing the adsorbent takes a long time, which has presented a big problem of workability. Particularly, to determine the moisture content with high accuracy, it is desirable to replace the adsorbent with fresh material either for each series of determinations or daily. Thus, a filter allowing the adsorbent to be conveniently replaced in a short time has also been necessary from the viewpoint of a highly accurate determination of moisture content.

Further, conventional filters are made of stainless steel. Because it is desirable to heat the filter in service, a heater is wound round the holder made of stainless steel. Thus, the inside of the filter cannot be inspected for contamination or change in color of the adsorbent.

Therefore, the purposes of the present invention are to offer a filter for the moisture meter that allows the adsorbent in the filter to be conveniently replaced with fresh material in a short time without twisting the tube connected to the top cover, and to offer an integral type filter whose inside can be checked and which is equipped with a heater.

In a moisture adsorption unit, shutting off the atmospheric moisture is a requisite to improving the determination accuracy. However, with the moisture adsorption unit as stated above, to meet such a requirement, the cell base and the cell body, and the cell body and the cap are connected to each other by tightening them with two or more gaskets (O-rings) stacked one upon another.

However, such a connection means imposes a great load on the weighing arm in the electronic weighing machine during mounting and removing of the cap and cell body. This may result in variations of the measurement by the electronic weighing machine, and in the worst case, failure of the electronic weighing machine itself.

Further, the conventional cell body is made of stainless steel, which makes it impossible to check for contamination of the adsorbent from the outside and to know the proper time of replacement.

Therefore, the purpose of the present invention is to offer a moisture adsorption unit for the moisture meter that is not only configured so that the cell body can be separated from the cell base connected with the carrier gas introduction tube, but also configured so that no great load is imposed on the weighing arm in the electronic weighing machine in mounting and removing of the cap and the cell body.

SUMMARY OF THE INVENTION

The electronic weighing machine for the moisture meter is used with the moisture meter which is equipped with a heating section for introducing the carrier gas into it and heating the test sample, a moisture adsorption section for adsorbing the vaporized moisture from the carrier gas flowing out of the heating section, and an electronic weighing section for determining the increase in mass of the moisture adsorption section. The electronic weighing section has a test sample weighing section and a section for measuring the mass of the collected vaporized moisture in the weighing arm 6a of the electronic weighing unit 6d.

BRIEF DESCRIPTION OF THE DRAWINGS

FIG. 2 is a sectional view of the electronic weighing machine as an example of an embodiment of the present invention.

FIG. 3 is a schematic plan view of the electronic weighing machine as an example of an embodiment of the present invention.

FIG. 5 is an exploded sectional view of the heating section as an example of an embodiment of the present invention.

FIG. 6 is a sectional view of the heating section as an example of an embodiment of the present invention (when a determination is made).

FIG. 11 is a sectional view of the moisture adsorption section as an example of an embodiment.

FIG. 12 is a perspective view of the moisture adsorption section as an example of an embodiment of the present invention.

FIGS. 13A and 13B are sectional views of the moisture adsorption section as an example of embodiment when a determination is made and not made.

DETAILED DESCRIPTION OF THE INVENTION

Figure 1:
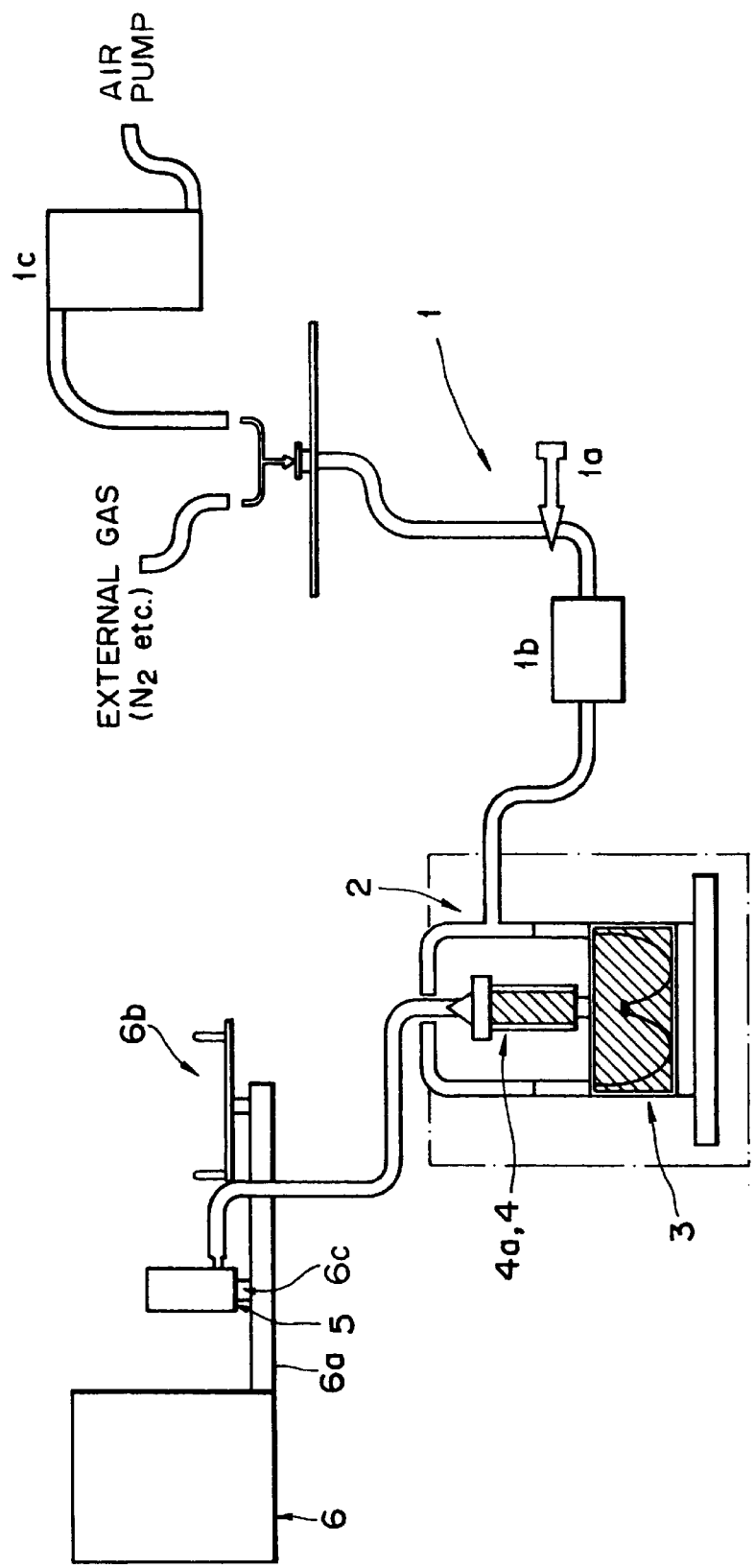
FIG. 1 is a block diagram illustrating the path of the fluid system in the moisture meter to which the present invention is applied, and shows the function of the fluid system.

To achieve the objectives stated above, the present invention is characterized in that it provides an electronic weighing machine for the moisture meter which determines the moisture content of the test sample by vaporizing the moisture in the tests ample by heating, carrying it with the carrier gas, and collecting and measuring only the vaporized moisture. In the weighing arm of the electronic weighing unit in the electronic weighing machine, a test sample weighing section and a section for measuring the mass of the collected vaporized moisture are provided.

The present invention is also characterized in that the moisture meter is equipped with a control section for adjusting the flow rate of the carrier gas, a heating section for introducing the carrier gas (the flow rate of which is adjusted by the control section) and for heating and drying the test sample, a filter section for removing the gases other than the vaporized moisture in the test sample that are produced in the heating section, a moisture adsorption section for adsorbing only the moisture in the test sample that is vaporized by heating and drying, and an electronic weighing section for determining the increase in mass of this moisture adsorption section. The heating section is equipped with a one-end-opened cylindrical heating tube vertically installed so that the open end is directed downward.

In addition, the heating section has carrier gas introduction ports and a carrier gas flowing-out port connected with the filter section at the top closed end of the heating tube, and it is desirable that the heating tube be heated and the carrier gas be introduced from the carrier gas introduction ports to always pressurize the inside of the heating section to a pressure higher than the atmospheric pressure.

Further, in the heating section, a sealing member is provided at the bottom of the bottom open end of the heating tube. It is desirable that the heating section be configured so that the heating tube can be sealed by joining the sealing member with the circumferential projection on the heating tube cover placed under the bottom of the heating tube when the determination of increased mass is not made, and by joining the sealing member with the flange of the sample tray loaded with the test sample when the determination is made.

For the electronic weighing section, a configuration in which an electronic weighing unit for determining the increase in mass of the moisture adsorption section, and also for measuring the mass of the test sample is provided. The filter section consists of a hollow cylindrical holder, a filter body charged with adsorbent, and a cover mounted to the holder. The filter body is inserted into the holder, and fixed and enclosed by engaging the projections in the upper portion of the holder with the lead grooves provided in the cover.

The moisture adsorption section consists of a base to be joined to the electronic weighing section, a cell body charged with adsorbent, and a cap confining the cell body. It is desirable that the base and the cell body, and the cell body and the cap be joined and connected with each other only by fitting the tapered projection to the tapered recess. It is desirable that, before the heating section, a dividing section for introducing the carrier gas into the heating section from at least two introduction ports be provided.

To achieve another objective stated above, the present invention is characterized in that the moisture meter is equipped with a control section for adjusting the flow rate of the carrier gas; a heating section for introducing the carrier gas (the flow rate of which is adjusted by the control section) and for heating and drying the test sample, a filter section for removing the gases other than the vaporized moisture in the test sample that are produced in the heating section, a moisture adsorption section for adsorbing only the moisture in the test sample that is vaporized by heating and drying, and an electronic weighing section for determining the increase in mass of this moisture adsorption section. Before the heating section, a dividing section for introducing the carrier gas into the heating section from at least two introduction ports is provided.

In addition, it is desirable that the electronic weighing section have an electronic weighing unit for determining the increase in mass of the moisture adsorption section, and also for measuring the mass of the test sample.

Further, the filter section consists of a hollow cylindrical holder, a filter body charged with active carbon, and a cover mounted to the holder, and can be configured so that filter body is inserted into the holder, and fixed and enclosed by engaging the projections in the upper portion of the holder with the lead grooves provided in the cover. The moisture adsorption section consists of a base to be joined to the electronic weighing section, a cell body charged with adsorbent, and a cap confining the cell body. It is desirable that the base and the cell body, and the cell body and the cap be joined and connected with each other only by fitting the tapered projection to the tapered recess.

The filter section and moisture adsorption section can be made of glass.

To achieve another objective stated above, the present invention is characterized in that the filter for the moisture meter is equipped with a heating section for introducing the carrier gas and heating the test sample, a moisture adsorption section for adsorbing only the moisture in the test sample that is vaporized by heating, and an electronic weighing section for determining the increase in mass of this moisture adsorption section.

The filter is provided before the moisture adsorption section, having a hollow cylindrical holder, a filter body charged with adsorbent, and a cover mounted to the holder, and is configured so that, at the top of the cover, a tube for passing the carrier gas is provided, and the filter body is inserted into the holder and fixed and enclosed by engaging the projections in the upper portion of the holder with the lead grooves provided in the cover.

In addition, it is desirable that, for the filter, a heater is loaded on the surface of the holder. It is desirable that the filter be made of glass, and the heater loaded on the surface of the holder be transparent.

Further, it is desirable that said adsorbent be active carbon.

To achieve another objective stated above, the present invention is characterized in that it provides a moisture adsorption unit for the moisture meter which determines the moisture content of the test sample by vaporizing the moisture in the test sample by heating, carrying it with the carrier gas, and collecting and measuring only the vaporized moisture. The moisture adsorption unit is joined to the weighing arm in the electronic weighing machine, having a base to be connected with a tube for introducing the carrier gas, a cell body charged with adsorbent for collecting only the vaporized moisture, and a cap for confining the cell body. The base and the cell body, and the cell body and the cap can be joined and connected with each other only by fitting the tapered projection to the tapered recess.

In addition, it is desirable that, with the cell body, the atmosphere be able to be shut off only by turning the cap.

Further, it is desirable that the cell body be filled with an adsorbent which changes its color as the moisture is collected. In this case, it is desirable that the cell body be made of clear glass.

With the present invention, the means allow measuring of not only the amount of the moisture contained in the test sample, but also the mass of the test sample itself. Thus, there is no need for separately installing a highly accurate weighing machine outside the moisture meter, and moving the test sample outside the moisture meter during moisture content determination. Therefore, errors due to the measuring environment such as the atmospheric moisture can be prevented.

With the present invention, the heating section of the moisture meter is equipped with an upright and cylindrical heating tube. Thus, the atmosphere can be prevented from entering the heating tube during insertion of the test sample, and the moisture content can be determined under the conditions which minimize the effect of the atmospheric moisture.

With the present invention, by always heating the heating tube and always introducing the carrier gas from the carrier gas introduction ports, the inside of the heating section is always pressurized to a pressure higher than the atmospheric pressure, and the heating tube is always sealed with the heating tube cover and the sample tray. Thus, the atmosphere is completely prevented from entering the heating tube, and the moisture content can be determined with higher accuracy.

In addition, with the means of the present invention, the electronic weighing section provided for the moisture meter can measure not only the amount of the moisture contained in the test sample, but also the mass of the test sample itself. This eliminates the need for separately installing a highly accurate weighing machine, and moving the test sample outside the moisture meter. Therefore, errors due to the measuring environment such as the atmospheric moisture can be prevented.

Further, with the present invention, a dividing section for dividing the carrier gas into at least two is provided, and at the top of the heating tube, two or more introduction ports for introducing the divided flows of the carrier gas are provided. Thus, introduction of the carrier gas into the heating tube can be made from more than one port. Therefore, the vaporized moisture and gases produced from the heated test sample can be effectively carried by the carrier gas, and the amount of the vaporized moisture can be measured in a short time with high accuracy.

With the present invention, a dividing section for dividing the carrier gas into at least two portions is provided. Thus, introduction of the carrier gas into the heating tube can be made from more than one port. Therefore, the vaporized moisture and gases produced from the heated test sample can be effectively carried by the carrier gas, and the amount of the vaporized moisture can be measured in a short time with high accuracy.

With the present invention, by engaging the projections in the upper portion of the filter holder with the lead grooves provided in the cover, the filter body charged with the adsorbent can be fixed and enclosed. Thus, during replacement of the adsorbent in the filter with fresh material, the cover can be easily mounted and removed without twisting the tube connected to the cover, which allows the adsorbent to be conveniently replaced with fresh material in a short time.

In addition, with the present invention, the filter can be made of glass, and the heater loaded on the surface of the holder can be transparent. Thus, the contamination inside the filter and a color change of the adsorbent can be detected from the outside.

With the moisture adsorption unit of the present invention, the base connected with the carrier gas introduction tube and the cell body, and the cell body and the cap can be joined and connected with each other only by fitting the tapered projection to the tapered recess. Thus, the cell body and the cap can be mounted and removed without imposing a load on the weighing arm.

In addition, with the cell body of the present invention, the atmosphere can be shut off only by turning the cap. Thus, no load is imposed on the weighing arm during such shutting.

Further, with the present invention, the adsorbent with which the cell body is charged changes its color as the moisture is collected. Thus, the proper time when the adsorbent is to be replaced with fresh material can be known from this change in color, and because the cell body is made of glass, such a change in color can be known from the outside of the cell body.

EXAMPLES OF EMBODIMENTS

Here is a detailed description of the present invention on the basis of the example of embodiment as shown in drawings.

FIG. 1 shows an example of AN embodiment of the electronic weighing machine for the moisture meter on the present invention, with a block diagram illustrating the path of the fluid system in the moisture meter to which the electronic weighing machine of the present invention is applied, and illustrates the function of it. In FIG. 1, the reference No. 1 denotes the control section for controlling the carrier gas; 2 the dividing section for dividing the flow of the controlled carrier gas into two portions; 3 the heating section for introducing the carrier gas from the dividing section 2 and heating and drying the test sample; 4 the filter section for purging the carrier gas flowing out of the heating section 3, carrying the vaporized moisture and gases produced by heating, of the gases other than the vaporized moisture; 5 the moisture adsorption section for adsorbing only the vaporized moisture from the carrier gas carrying the vaporized moisture, flowing out of the filter section 4; and 6 the electronic weighing section for determining the increase in mass of the moisture absorption section 5. As required, a dry unit 1c to dry the moisture in the carrier gas is provided before the control section 1. It is desirable that the tubes in which the carrier gas flows be made of Teflon.

The control section 1 consists of a needle valve 1a for adjusting the flow rate of the carrier gas made of an inert gas, such as nitrogen and helium, or dry air produced by drying the air; and a flow sensor 1b for determining the flow rate of the carrier gas delivered to the heating section. When dry air produced by drying the air is used as the carrier gas, a dry unit is provided before the needle valve 1a.

The dividing section 2 is not always necessary in the moisture meter to which the electronic weighing machine of the present invention is applied. However, to positively deliver the carrier gas onto the surface of the test sample, and to thoroughly carry the vaporized moisture to the moisture adsorption section 5, it is desirable to divide the flow of the carrier gas into at least two portions, preferably two or three portions, before introducing it into the heating section 3.

FIG. 2 gives a sectional view of the electronic weighing section 6, and FIG. 3 a schematic plan view of it. In these figures, the electronic weighing section 6 is equipped with a test sample weighing section 6b and a section 6c for measuring the mass of the collected vaporized moisture in the weighing arm 6a of the electronic weighing unit 6d. The test sample weighing section 6b and the vaporized moisture mass measuring section 6c may be located anywhere. However, from the viewpoint of structure, it is desirable that the test sample weighing section 6b be located in the end portion of the weighing arm 6a.

The test sample is weighed by contacting the weighing shafts 6e provided on the top of the test sample weighing section 6b with the sample tray 3h, and measuring the mass of the sample tray 3h (before and after the test sample is put on it) with the test sample weighing section 6b.

On the top of the vaporized moisture mass measuring section 6c, the moisture adsorption section 5 is provided to determine the increase in mass of the adsorbent in the moisture adsorption section as the amount of the vaporized moisture in the test sample.

Figure 4:
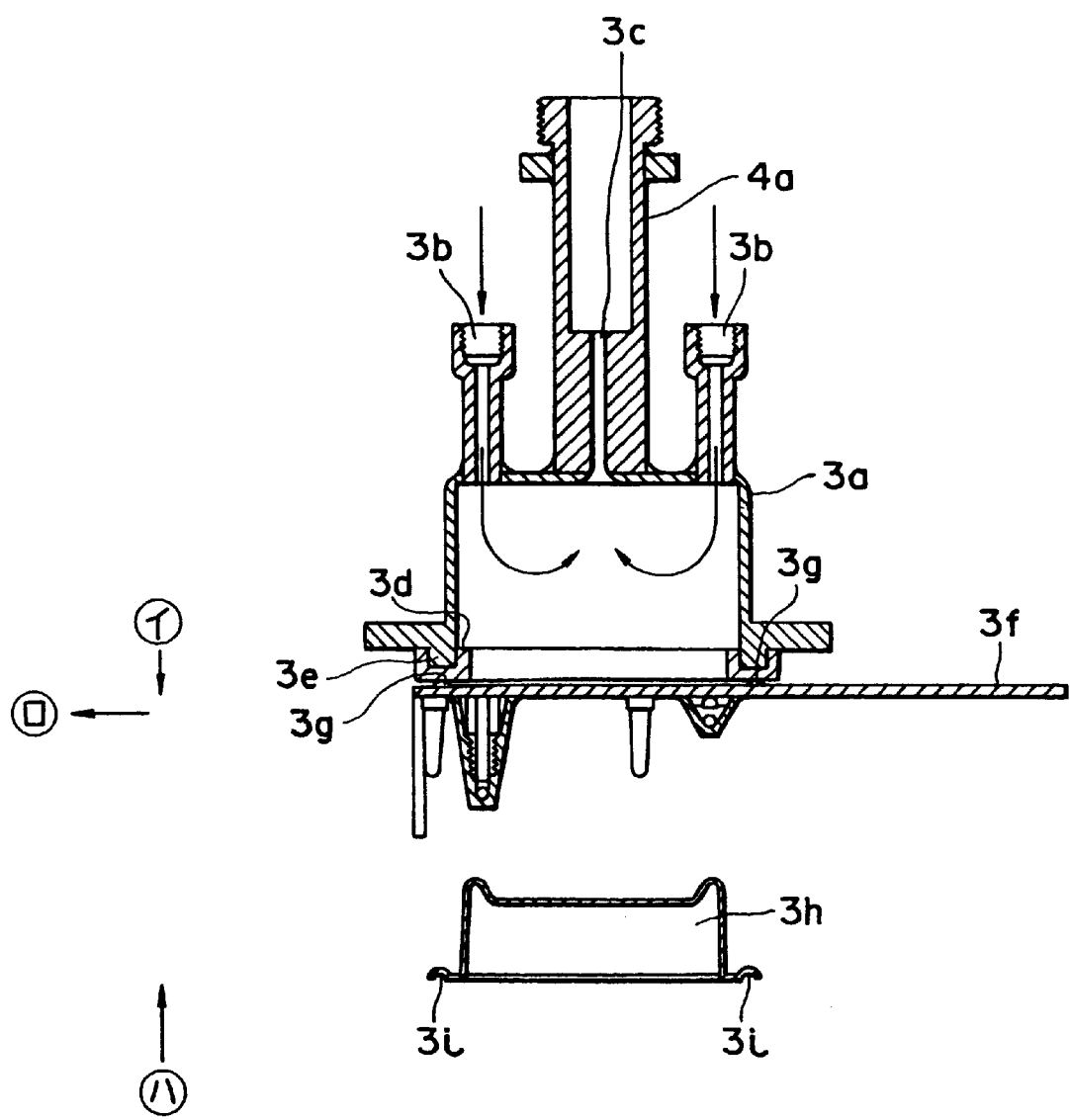
FIG. 4 is a sectional view of the heating section as an example of an embodiment of the present invention (when a determination is not made).

FIGS. 4 to 7 give figures showing the heating section 3 and the holder 4a for the filter section 4. Here, FIGS. 4 and 5 give sectional views of the heating section 3 and the holder 4a for the filter section 4, and the heating section 3 is equipped with an upright and cylindrical heating tube 3a. On the top of the tube 3a, two carrier gas introduction ports 3b and a carrier gas flowing-out port 3c connecting to the filter section 4 are provided. On the periphery of the heating tube 3a, a heater is loaded. To allow the inside of the heating tube 3a to be simply inspected, it is desirable that the heating tube 3a and the heater to be loaded be transparent, and, particularly, that the heating tube 3a be made of glass also from the viewpoint of resistance to heat.

The number of carrier gas introduction ports 3b does not always need to be two, and may be one. However, when the flow of the carrier gas is divided in the dividing section 2 as stated above, the number of carrier gas introduction ports is made equal to the number of divisions of the flow of the carrier gas. It is desirable that the connection between the carrier gas introduction port 3b and the Teflon tube be made of nylon.

As shown in FIGS. 4 and 5, at the bottom of the heating tube 3a, a sealing member 3d is mounted along the bottom section 3e of the heating tube. The sealing member 3d may be made of any material, if it is heat resistant and not water absorbent. However, it is desirable that the sealing member 3d be made of a fluororubber because of its excellent heat resistance and adhesion, and freedom from water absorption.

FIG. 4 shows the state of the heating section when a determination is not made, and the bottom of the heating tube 3a is hermetically sealed by the heating tube cover 3f. The heating tube cover 3f is provided with a circumferential projection 3g, which can be pressed against the sealing member 3d to hermetically seal the heating tube in joining.

On the other hand, FIG. 6 is a sectional view of the heating section 3 and the holder 4a for the filter section 4 when a determination is made. At the bottom of the heating tube 3a, a sample tray 3h is loaded so that the flange 3i of the sample tray 3h is pressed against the sealing member 3d to hermetically seal the heating tube in the same manner as when a determination is not made.

Before the test sample is tested, the heating tube cover 3f is slightly moved in the direction of arrow "T" and then moved in the direction of arrow "□". If, in this state, the heating tube is heated and the carrier gas is introduced into it, the difference between the inside and outside pressures prevents the atmosphere from entering the heating tube. Thus, the test sample can be inserted into it without being affected by the atmospheric moisture. Then the sample tray 3*h* is lifted in the direction of arrow "∧", resulting in the flange 3*i* of the sample tray 3*h* tightly contacting the sealing member 3*d* at the bottom of the heating tube 3*a*.

Figure 7:
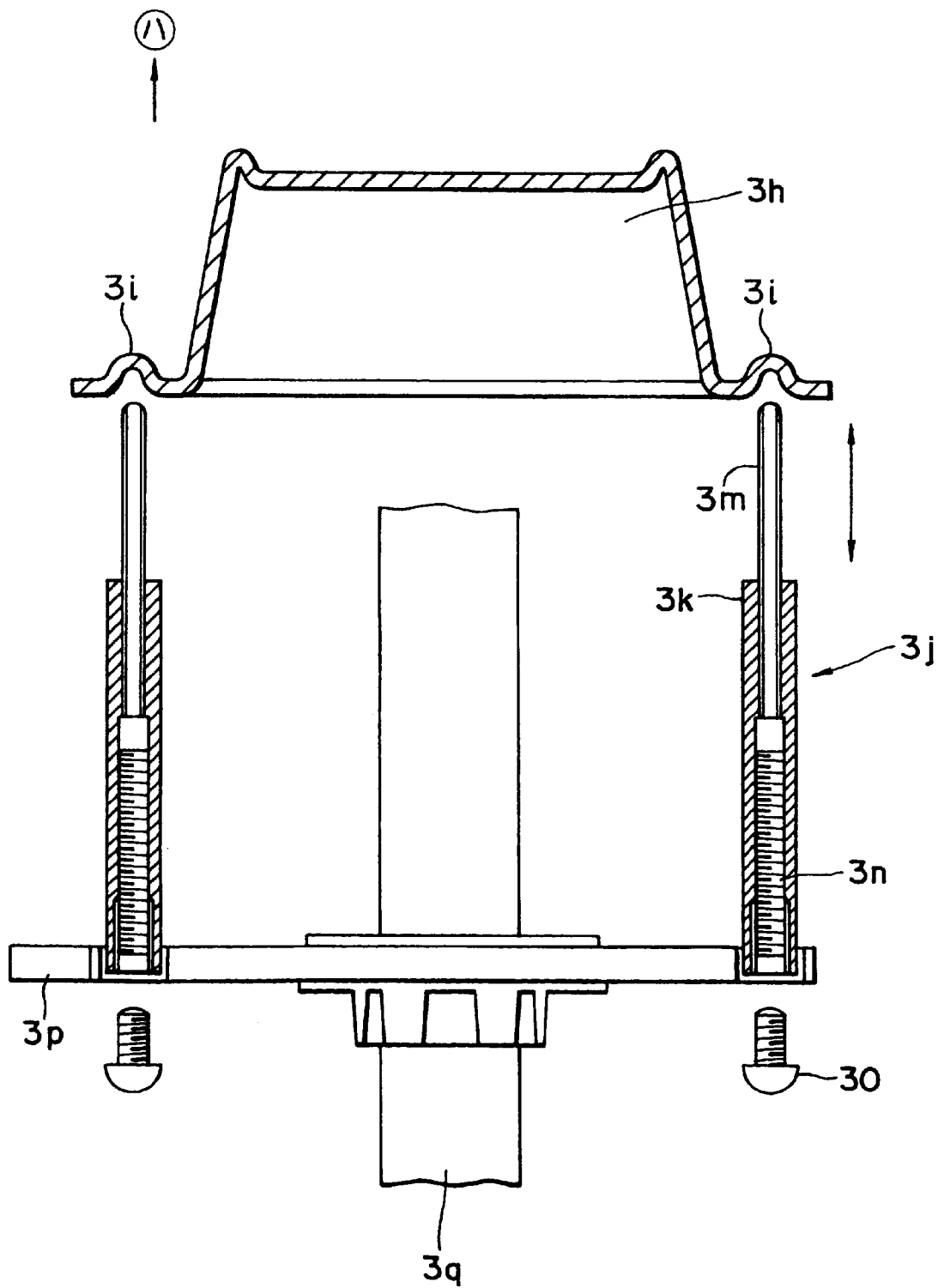
FIG. 7 is a drawing illustrating the sample tray lifting mechanism when a determination is made.

FIG. 7 illustrates lifting of the sample tray 3*h*. The sample tray 3*h* is lifted by the lifting shafts 3*j*. The lifting shafts 3*j* are mounted to the disk 3*p* with screws 3*o*. The disk 3*p* can be raised and lowered by turning the screw 3*q*. The lifting shaft 3*j* consists of a base shaft 3*k*, a shaft 3*m* sliding in the inside of the base shaft 3*k*, and a spring 3*n*. Because the lifting shaft 3*j* has a spring, it can be set to apply the load required for hermetically sealing the sample tray if the lifting stop position accuracy varies, and the lifting pressure can be simply increased or decreased by changing the thread length of the screw 3*o*.

Figure 8:
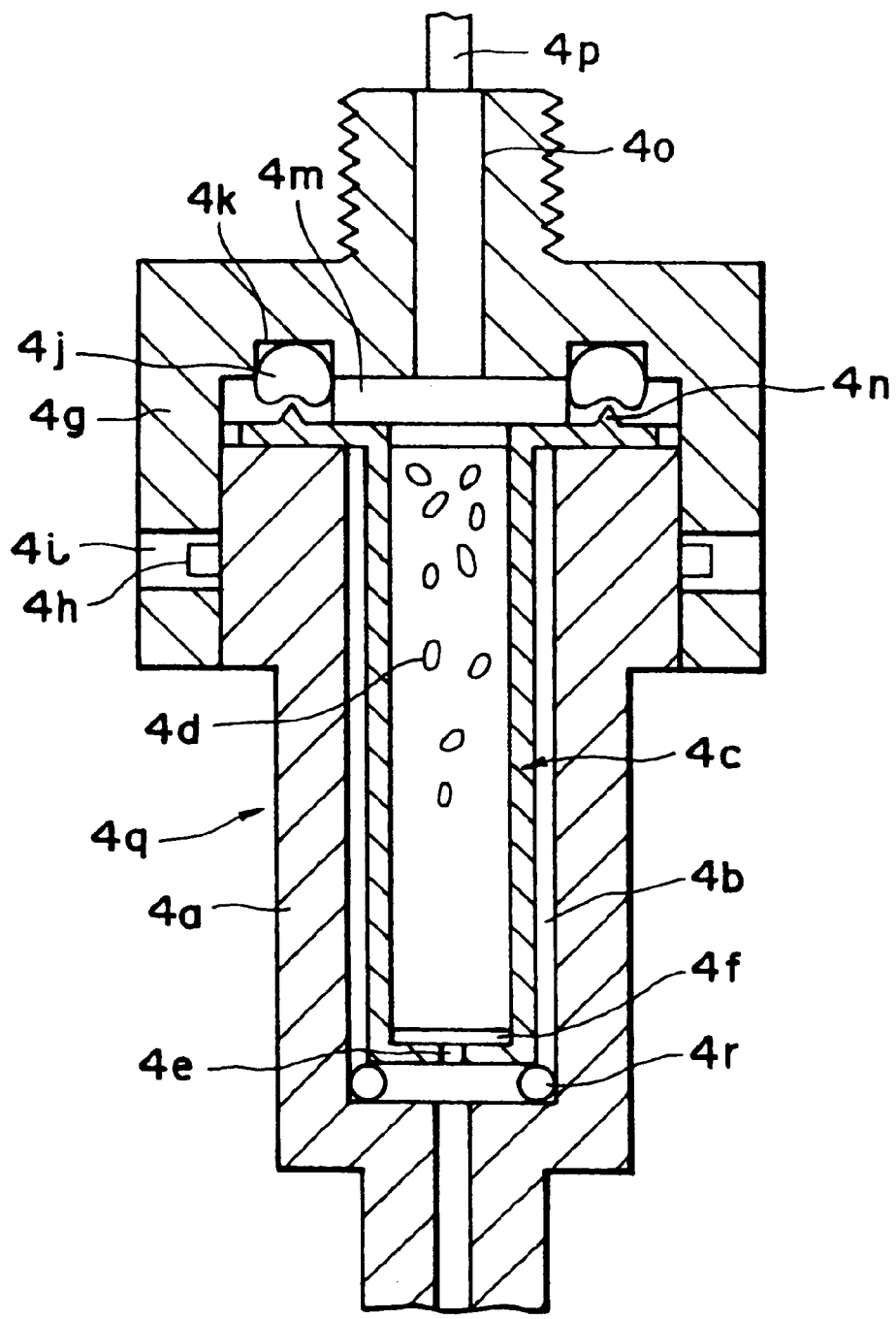
FIG. 8 is a sectional view of the filter section as an example of an embodiment.

FIG. 8 gives a sectional view of the filter section 4. In this figure, the filter 4 has a holder 4*a*, an insertion section 4*b*, a filter body 4*c*, and activated carbon 4*d* with which the filter body 4*c* is charged. The filter body 4*c* has a hole 4*e* connecting to the insertion section 4*b*, and at the bottom of the filter body 4*c*, a mesh plate 4*f* is placed. At the periphery of the holder 4*a*, a heater 4*q* is installed. From the viewpoint of easier checking of the filter for contamination and others, it is desirable that the holder 4*a* and the heater 4*q* be made of glass. For allowing highly accurate measurement to be made, it is desirable to daily replace the activated carbon with fresh material.

Figure 9:
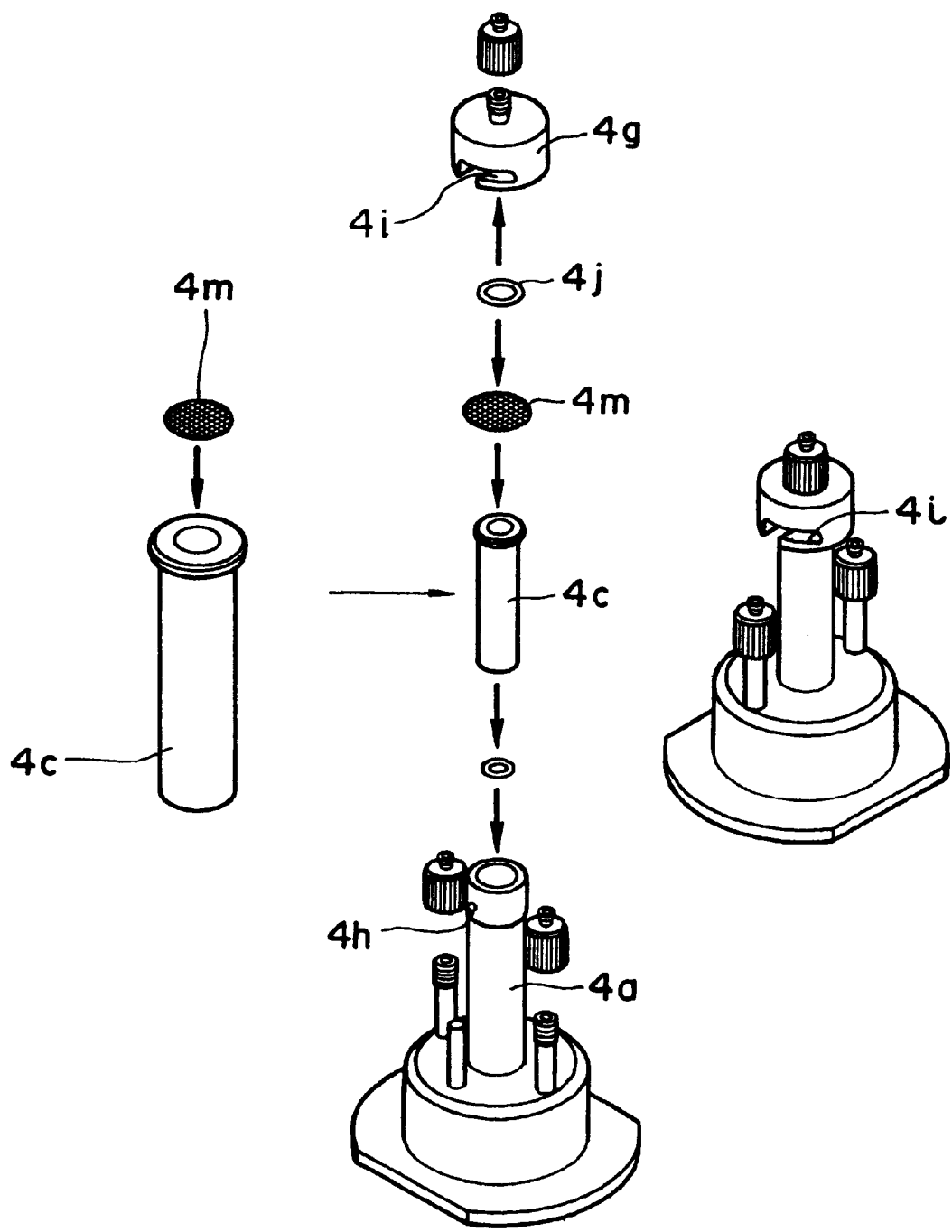
FIG. 9 is an exploded view illustrating how to replace the filter body of the present invention with a new one.
Figure 10:
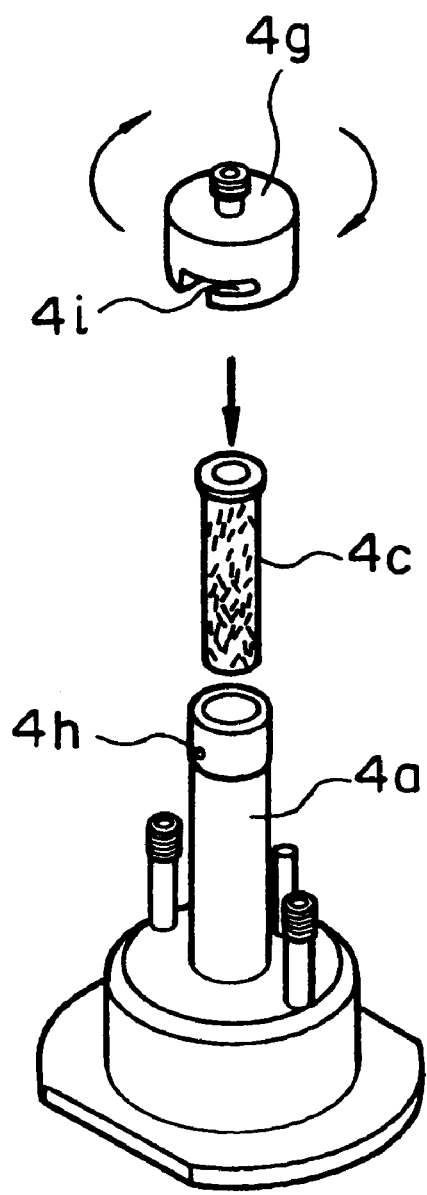
FIG. 10 is an exploded view illustrating how to replace the filter body of the present invention with new a one.

At the top of the holder 4*a*, a cover 4*g* is provided, and at the top of the cover 4*g*, a tube fitting 4*o* for passing the carrier gas, and a tube 4*p* are provided. Replacement of the filter body with a new one is performed as illustrated in FIG. 9, and assembling the holder 4*a* with the cover 4*g* for fixing the filter body 4*c* is made by engaging the projections 4*h* in the upper portion of the holder 4*a* with the lead grooves 4*i* provided on the side of the cover 4*g*, as shown in FIG. 10. Because such a fixing method is adopted, replacement of the filter body 4*c* with a new one can be made with extreme ease, and when removing the cover 4*g* for replacement, the tube 4*p* is not twisted. Thus, the tube 4*p* is free from cracks or other damages that would be caused if the surface were twisted, and the cover 4*g* can be removed from the holder 4*a* with the tube 4*p* being kept jointed to the cover 4*g*, which results in a substantial improvement in workability.

At the rear of the cover 4*g*, a groove 4*k* for accommodating an O-ring 4*j* is provided. The top of the filter body 4*c* is flanged, and the flange 4*n* tightly contacts with the O-ring 4*j* accommodated in the groove 4*k* in the rear surface of the cover 4*g*. At the top of the filter body 4*c*, a mesh plate 4*m* is provided between the flange 4*n* and the cover 4*g*, and at the bottom of the filter body 4*c*, an O-ring 4*r* is provided between 4*a* and 4*c*.

FIG. 11 gives a sectional view of the moisture adsorption section 5, while FIG. 12 is a perspective view of the moisture adsorption section 5 being mounted to the weighing arm 6*a*. The moisture adsorption section 5 has a base 5*b* to which a carrier gas introduction tube 5*a* is connected, and a cell body 5*d* which is charged with an adsorbent 5*c* for adsorbing the vaporized moisture. The base 5*b* is provided with a fitting 5*e* to which the tube 5*a* is connected, a hole 5*f*, and a tapered projection 5*g* to which the cell body 5*d* is fitted. The base 5*b* having the projection 5*g* is mounted to the weighing arm 6*a* in the electronic weighing section 6. The cell body 5*d* has a tapered recess 5*h* to be fitted to the tapered projection 5*g* for joining it to the base 5*b*. In the cell body 5*d*, a disc 5*i* made of Teflon is installed which is holed to allow the carrier gas to flow into the cell body 5*d*.

At the top of the cell body 5*d*, a cap 5*j* is loaded. The cap 5*j* is provided with more than one discharge port 5*k* arranged symmetrically in the horizontal direction, which can connect to the discharge ports 5*o* given in the tapered recess 5*m* provided at the top of the cell body. It is desirable that the discharge ports 5*o* be provided at right angles to the carrier gas introduction tube 5*a*. The cap 5*j* is joined to the cell body 5*d* by fitting the tapered recess 5*m* at the top of the cell body to a tapered projection 5*n* at the bottom of the cap 5*j*. FIG. 13A shows the state of the moisture adsorption section when a determination is made, and FIG. 13B shows the state when it is not made. The discharge ports 5*k* in the cap 5*j* can be easily connected to and disconnected from the discharge ports 5*o* given in the tapered recess 5*m* provided at the top of the cell body by turning the cap 5*j* through an angle of 90 degrees, which allows the carrier gas to be easily discharged, and the atmosphere to be shut off with ease. Thus, the cell body 5*d* can be jointed to the base 5*b* or the cap 5*j* simply by fitting the tapered projection to the tapered recess, and the tube 5*a* is joined to the base 5*b*. Therefore, during replacement of the cell body with new one, no great external force is applied to the electronic weighing section 6, resulting in the electronic weighing machine being protected against damage. The cell body 5*d* and the adsorbent 5*c* are made of any material. However, in order to easily know the absorbent with fresh material, it is desirable that the cell body 5*d* be made of glass, and that the adsorbent 5*c* have such a property that it changes its color as the, moisture is collected. Among the adsorbents having such a property, molecular sieves are more desirable, and Molecular Sieve 3A is the most desirable. From the viewpoint of ease of removing and adhesion, it is desirable that the tapered projection of the base 5*b* and that of the cap 5*j* be made of Teflon.

It is to be noted that the weighing arm 6*a* in the electronic weighing section 6 is provided with a moisture mass measuring section 6*c* and a test sample weighing section 6*b* to allow measuring not only of the mass of the vaporized moisture, but also of the mass of the test sample itself.

For the heating section in the present invention, no restrictions are provided, and there is no significant difference between the heating section equipped with a vertical heating tube and that with a horizontal one. However, it is desirable that, in order to prevent the atmosphere from entering the heating tube during insertion of the test sample, and in order to determine the moisture content under the conditions which minimize the effect of the atmospheric moisture, the heating section be equipped with a vertical heating tube.

In addition, the electronic weighing section 6 has an electronic weighing unit that is equipped with a test sample weighing station and a section for measuring the mass of the vaporized moisture in the weighing arm of it.

As described above, the present invention is configured so that the electronic weighing machine for the moisture meter can measure not only the amount of the vaporized moisture, but also the mass of the test sample itself. Thus, there is no need for separately installing a highly accurate weighing machine outside the moisture meter, or for moving the test sample itself outside the moisture meter in making measurement. Therefore, the equipment can be simplified and errors due to the measuring environment can be prevented. Particularly, the amount of the moisture can be measured without being affected by the atmospheric moisture, which allows the measuring accuracy to be substantially improved and a trace amount of moisture in the test sample to be measured with high accuracy.

The present invention is also configured to provide a vertical heating tube in the heating section of the heat drying type moisture meter. Thus, the atmosphere can be prevented from entering the heating tube during insertion of the test sample into it. In addition, by always pressurizing the inside of the heating tube and hermetically sealing it the atmosphere can be completely shut off, and the amount of the moisture can be measured without being affected by the atmospheric moisture. This allows the measuring accuracy to be substantially improved and an extremely low moisture content of 10 ppm of the test sample to be measured with high accuracy.

When the moisture meter uses an electronic weighing section having a weighing arm that allows measuring of not only the mass of the moisture, but also the mass of the test sample itself, there is no need for separately installing a highly accurate weighing machine, or for moving the test sample outside the moisture meter. Therefore, the equipment can be simplified and errors due to the measuring environment can be prevented.

When a dividing section for dividing the flow of the carrier gas into two or more portions before it is introduced into the heating section is provided, the vaporized moisture and gases produced in the heating section can be effectively carried by the carrier gas flowing in from more than one port. Therefore, a wide range of moisture content can be determined whether the test sample is solid or liquid, and the amount of the vaporized moisture can be measured in a short time with high accuracy.

As a good example of an embodiment of the present embodiment, the filter body in the filter section can be easily replaced with a new one without removing the tube from the cover, which results in an improvement in workability. Particularly, considering that it is desirable to daily replace the filter body with a new one for a highly accurate determination, the improvement in workability with the present invention is extremely important for making the moisture content determination more effective.

The cell body can be loaded only by fitting the tapered projection to the tapered recess. Therefore, during replacement of the cell body with new one, no great external force is applied to the arm and other parts in the electronic weighing section, resulting in the electronic weighing machine being protected against damage.

The present invention also provides a dividing section for dividing the flow of the carrier gas into two or more portions before it is introduced into the heating section. Thus, the vaporized moisture and gases produced in the heating section can be effectively carried by the carrier gas flowing in from more than one port. Therefore, a wide range of moisture content can be determined whether the test sample is solid or liquid, and the amount of the vaporized moisture can be measured in a short time with high accuracy.

When the moisture meter uses an electronic weighing section having a weighing unit that allows measuring of not only the mass of the moisture, but also the mass of the test sample itself, there is no need for separately installing a highly accurate weighing machine, or for moving the test sample outside the moisture meter. Therefore, the equipment can be simplified and errors due to the measuring environment can be prevented.

As a good example of an embodiment of the present embodiment, the filter body in the filter section can be easily replaced with a new one without removing the tube from the cover, which results in an improvement in workability. Particularly, in consideration of that it is desirable to daily replace the filter body with a new one for a highly accurate determination, the improvement in workability with the present invention is extremely important for making the moisture content determination more effective.

The cell body can be loaded only by fitting the tapered projection to the tapered recess. Therefore, in replacement of the cell body with a new one, no great external force is applied to the arm and others in the electronic weighing section, resulting in the electronic weighing machine being protected against damage.

The present invention is also configured so that, by engaging the projections in the upper portion of the filter holder with the lead grooves provided in the cover, the filter body charged with the adsorbent can be fixed and enclosed. Thus, in replacement of the adsorbent in the filter with fresh material, the cover can be easily mounted and removed without twisting the tube connected to the cover, which allows the adsorbent to be conveniently replaced with fresh material in a short time. Particularly, when the moisture content must be determined with high accuracy, it is desirable to replace the adsorbent with fresh material for a series of determinations or daily. From this viewpoint, the improvement in workability in replacement of the adsorbent with fresh material by using the filter of the present invention is extremely important for making the moisture content determination more effective.

With the present invention, a configuration in which the filter is made of glass, and the heater loaded on the surface of the holder is transparent can be adopted. Thus, in such a case, the contamination inside the filter and a color change of the adsorbent can be detected from the outside, which allows the moisture content to be determined with higher accuracy.

The present invention is also configured so that the base of the moisture adsorption unit and the cell body, and the cell body and the cap can be joined and connected with each other only by fitting the tapered projection to the tapered recess. Thus, the cell body and the cap can be mounted and removed without imposing a load on the weighing arm. Although such a simple method of loading and unloading is used, the moisture adsorption unit of the present invention offers an excellent atmosphere shutting effect, and with such a fitting portion, no leakage of the carrier gas carrying the vaporized moisture is caused, which allows the moisture content to be determined with extremely high accuracy.

With the cell body of the present invention, a switch from discharging the carrier gas to shutting off the atmosphere or vice versa is performed only by turning the cap loaded on the top of the cell body. Thus, no load is imposed on the weighing arm in switchover.

With the present invention, the adsorbent with which the cell body is charged changes its color as the moisture is collected, and the cell body is made of glass to allow the change in color to be identified from the outside. Thus, the proper time when the adsorbent is to be replaced with fresh material can be known, resulting in an improvement in determination accuracy of the moisture meter.

What is claimed is:

1. A moisture meter apparatus comprising:
    a heating component for heating a test sample by using carrier gas so as to vaporize moisture in the test sample such that the carrier gas carries the vaporized moisture;
    a moisture adsorption component for adsorbing only the vaporized moisture carried by the carrier gas; and
    an electronic weighing component having a weighing arm including a test sample weighing portion and a vaporized moisture mass measuring portion for measuring a mass of the vaporized moisture adsorbed by said moisture adsorption component.

2. A moisture meter apparatus comprising:
- a control component for adjusting a flow rate of a carrier gas supplied to a test sample;
- a heating component for heating and drying the test sample by introducing the carrier gas into said heating component at the flow rate adjusted by said control component so as to vaporize moisture in the test sample such that the carrier gas carries the vaporized moisture, said heating component including a cylindrical heating tube having an open end, said heating tube being vertically arranged such that said open end is directed downward;
- a filter component for removing gases produced in said heating component other than vaporized moisture from the carrier gas;
- a moisture adsorption component for adsorbing only the vaporized moisture carried by the carrier gas; and
- an electronic weighing component for determining an increase in a mass of said moisture adsorption component, said electronic weighing component including an electronic weighing unit for determining an increase in the mass of said moisture adsorption component and for measuring a mass of the test sample.

3. The apparatus of claim 2, wherein said heating component includes carrier gas inlet ports, and a carrier gas outlet port connected to said filter component at a closed end of said heating tube, wherein said control component adjusts the flow rate of the carrier gas introduced into said heating component through said carrier gas inlet ports so as to heat said heating component and so as to always maintain a pressure inside said heating component greater than an atmospheric pressure outside said heating component.

4. The apparatus of claim 2, further comprising a heating tube cover having a circumferential projection, and comprising a sample tray for supporting a test sample and having a flange, wherein said heating component includes a sealing member at a bottom of said open end of said heating tube, said sealing member of said heating component being adapted so as to be sealed by said circumferential portion of said heating tube cover when a moisture content determination is not being conducted, and said sealing member of said heating component being adapted so as to be sealed by said flange of said sample tray when a moisture content determination is being conducted.

5. The apparatus of claim 2, wherein said filter component includes a hollow cylindrical holder having an upper portion and projections extending from said upper portion, a filter body charged with adsorbent and fitted into said holder, and a cover mounted to said holder and having lead grooves, said cover being secured to said holder so as to enclose said filter body by engaging said lead grooves with said projections extending from said upper portion of said holder.

6. The apparatus of claim 2, wherein said moisture adsorption component includes a tapered base to be connected to said electronic weighing component, a cell body charged with adsorbent and having tapered ends, and a tapered cap for closing said cell body, said moisture adsorption component being constructed by fitting said tapered base and said tapered cap into said tapered ends of said cell body.

7. The apparatus of claim 2, wherein said heating component includes at least two carrier gas inlet ports, further comprising a dividing portion upstream of said heating component for dividing a flow of the carrier gas into at least two flow paths such that the carrier gas is introduced into said heating component through at least two carrier gas inlet ports.

8. A moisture meter apparatus comprising:
- a control component for adjusting a flow rate of a carrier gas supplied to a test sample;
- a heating component for heating and drying the test sample by introducing the carrier gas into said heating component at the flow rate adjusted by said control component so as to vaporize moisture in the test sample such that the carrier gas carries the vaporized moisture, said heating component including at least two carrier gas inlet ports;
- a dividing portion upstream of said heating component for dividing a flow of the carrier gas into at least two flow paths such that said carrier gas is introduced into said heating component through said at least two carrier gas inlet ports;
- a filter component for removing gases produced in said heating component other than vaporized moisture from the carrier gas;
- a moisture adsorption component for adsorbing only the vaporized moisture carried by the carrier gas; and
- an electronic weighing component for determining an increase in a mass of said moisture adsorption component, said electronic weighing component including an electronic weighing unit for determining an increase in the mass of said moisture adsorption component and for measuring a mass of the test sample.

9. The apparatus of claim 8, wherein said filter component includes a hollow cylindrical holder having an upper portion and projections extending from said upper portion, a filter body charged with activated carbon and fitted into said holder, and a cover mounted to said holder and having lead grooves, said cover being secured to said holder so as to enclose said filter body by engaging said lead grooves with said projections extending from said upper portion of said holder.

10. The apparatus of claim 8, wherein said moisture adsorption component includes a tapered base to be connected to said electronic weighing component, a cell body charged with adsorbent and having tapered ends, and a tapered cap for closing said cell body, said moisture adsorption component being constructed by fitting said tapered base and said tapered cap into said tapered ends of said cell body.

11. The apparatus of claim 8, wherein said filter component and said moisture adsorption component are formed of glass.

12. A moisture meter apparatus comprising:
- a heating component for heating a test sample by using carrier gas so as to vaporize moisture in the test sample such that the carrier gas carries the vaporized moisture;
- a moisture adsorption component for adsorbing only the vaporized moisture carried by the carrier gas;
- a filter component arranged upstream of said moisture adsorption component, said filter component including a hollow cylindrical holder having an upper portion and projections extending from said upper portion, a filter body charged with adsorbent and fitted into said holder, and a cover mounted to said holder and having lead grooves and a tube at a top of said cover for passing carrier gas therethrough, said cover being secured to said holder so as to enclose said filter body by engaging said lead grooves with said projections extending from said upper portion of said holder; and
- an electronic weighing component for determining an increase in a mass of said moisture adsorption component.

13. The apparatus of claim 12, wherein said filter component further includes a heater mounted on a surface of said holder.

14. The apparatus of claim 13, wherein said filter is formed of glass, and said heater is transparent.

15. The apparatus of claim 12, wherein said absorbent is activated carbon.

16. A moisture meter apparatus comprising:

a heating component for heating a test sample by using carrier gas so as to vaporize moisture in the test sample such that the carrier gas carries the vaporized moisture;

a moisture adsorption component for adsorbing only the vaporized moisture carried by the carrier gas, said moisture adsorption component having a tapered base to be connected to an inlet tube for introducing carrier gas into said moisture adsorption component, a cell body charged with adsorbent for adsorbing only the vaporized moisture and having tapered ends, and a tapered cap for closing said cell body, said moisture adsorption component being constructed by fitting said tapered base and said tapered cap into said tapered ends of said cell body; and an electronic weighing component for measuring a mass of the vaporized moisture collected by said moisture adsorption component, said electronic weighing component having a weighing arm, said moisture adsorption component being connected to said weighing arm.

17. The apparatus of claim 16, wherein said tapered cap has a plurality of discharge ports, said moisture adsorption unit being constructed such that said cell body can be isolated from an atmosphere outside said cell body by turning said cap so as to close said discharge ports.

18. The apparatus of claim 16, wherein said adsorbent is adapted to change color as the vaporized moisture is adsorbed.

19. The apparatus of claim 18, wherein said cell body is formed of clear glass.

* * * * *